(12) United States Patent
Keller et al.

(10) Patent No.: US 8,580,538 B2
(45) Date of Patent: Nov. 12, 2013

(54) ENZYMATIC PRODUCTION OF AN ETHYLENICALLY UNSATURATED GLYCOSIDE

(75) Inventors: Harald Keller, Ludwigshafen (DE); Katja Loos, Groningen (NL); Wouter Kloosterman, Groningen (NL)

(73) Assignee: BASF SE, Ludwigshafen (DE)

( * ) Notice: Subject to any disclaimer, the term of this patent is extended or adjusted under 35 U.S.C. 154(b) by 180 days.

(21) Appl. No.: 13/192,771

(22) Filed: Jul. 28, 2011

(65) Prior Publication Data

US 2012/0028308 A1 Feb. 2, 2012

Related U.S. Application Data

(60) Provisional application No. 61/368,710, filed on Jul. 29, 2010.

(51) Int. Cl.
*C12P 19/44* (2006.01)

(52) U.S. Cl.
USPC ............. 435/74; 435/195; 435/196; 435/197; 435/200; 435/201

(58) Field of Classification Search
USPC ........... 435/74, 195, 196, 197, 198, 199, 200, 435/201, 202, 203, 204, 208, 209
See application file for complete search history.

(56) References Cited

U.S. PATENT DOCUMENTS

2011/0313097 A1 12/2011 Keller et al.
2012/0016114 A1 1/2012 Keller et al.

FOREIGN PATENT DOCUMENTS

EP 0 226 563 A1 6/1987

OTHER PUBLICATIONS

Finch et al. Carbohydrate Research (1997) 303: 339-345.*
Fan et al. J. Biol. Chem. (1995) 270(30): 17723-17729.*
U.S. Appl. No. 13/264,634, filed Dec. 29, 2011, Keller, et al.
U.S. Appl. No. 13/192,761, filed Jul. 28, 2011, Keller, et al.
Shuichi Matsumura, et al., "Enzymatic synthesis of novel vinyl monomers bearing β-D-galactopyranoside residue", Makromol. Chem., Rapid Commun., vol. 14, 1993, pp. 55-58.
Iqbal Gill, et al, "Enzymatic Glycosylation in Plasticized Glass Phases: A Novel and Efficient Route to O-Glycosides", Angew. Chem. Int. Ed., vol. 39, No. 21, 2000, pp. 3804-3808.
F. van Rantwijk, et al., "Glycosidase-catalysed synthesis of alkyl glycosides", Journal of Molecular Catalysis B: Enzymatic, vol. 6, 1999, pp. 511-532.
Wen-Ya Lu, et al., "Facile Synthesis of Alkyl β-D-Glucopyranosides from D-Glucose and the Corresponding Alcohols Using Fruit Seed Meals", Practical Methods for Biocatalysis, Chapter 7.3, 2010, pp. 236-239.
James Lalonde, et al., "Immobilization of Enzymes", Enzyme Catalysis in Organic Synthesis, vol. I, 2002, pp. 163-184.

* cited by examiner

*Primary Examiner* — Susan Hanley
(74) *Attorney, Agent, or Firm* — Oblon, Spivak, McClelland, Maier & Neustadt, L.L.P.

(57) ABSTRACT

Ethylenically unsaturated glycosides of the formula I:

(I)

wherein n, A, X, $R^3$ and $R^4$ have the meanings given in the description are produced by reacting an ethylenically unsaturated alcohol of formula II:

(II)

with a saccharide of formula III:

(III)

in the presence of a glucosidase at a molar ratio of the alcohol to the saccharide of from 2:1 to 30:1 in the presence of a solvent mixture of water and 1,4-dioxane at a weight ratio of 0.1:1 to 9:1 and a weight ratio of solvent mixture to saccharide of from 3:1 to 30:1.

20 Claims, No Drawings

ENZYMATIC PRODUCTION OF AN ETHYLENICALLY UNSATURATED GLYCOSIDE

The invention relates to a method for producing an ethylenically unsaturated glycoside by reacting an ethylenically unsaturated alcohol with a saccharide in the presence of a glycosidase.

Polymers comprising sugar residues (saccharide copolymers) may share typical properties of saccharides such as good water solubility, high electrolyte stability, colloidal stability in hot water, strong interaction with surfaces such as cotton and non-toxicity. These specific properties open a variety of applications for such polymers. It is therefore of great interest to develop cost-effective methods for producing well-defined saccharide copolymers and their respective monomers. Such monomers may be polymerizable ethylenically unsaturated glycosides which result by glycosidic coupling a saccharide and an ethylenically unsaturated alcohol. The synthesis of such glycosides involves a number of challenges. There are many possibilities for the formation of positional isomers in which different hydroxyl groups of the saccharide become involved in bond formation. Further, there is the potential for the formation of different anomeric forms. Chemical synthesis of most monomers bearing sugar residues is therefore generally not feasible and results in poor yields of the desired monomer.

The application of enzymes has been considered an alternative approach for producing glycosidic monomers. In contrast to chemical synthesis, enzyme-catalyzed reactions of unprotected sugars usually yield a much more structurally homogeneous product due to their high stereoselectivity.

In general there are two approaches used for enzymatic synthesis of glycosides: thermodynamically controlled reverse hydrolysis and kinetically controlled transglycosylation. Transfer of glycosyl units to non-sugar compounds with primary hydroxyl groups by enzymatically catalyzed transglycosylation has been shown, for example, by S. Matsumura et al. (Makromol. Chem., Rapid Commun. 14:55-58, 1993). There have also been approaches to use glycosidases, which catalyze glycoside hydrolysis in vivo, for glycoside synthesis by reverse hydrolysis (see for example I. Gill and R. Valivety, Angew. Chem. Int. Ed. 39(21):3804-3808, 2000).

In the development of methods for glycosidase catalyzed synthesis of glycosides, difficulties have been encountered in finding optimum solvent conditions. On the one hand, favoring the thermodynamically controlled reverse hydrolysis requires the water content, or rather the thermodynamic water activity $a_w$, to be minimized. On the other hand, saccharides, which are generally readily water-soluble, are often scarcely soluble in organic media. Replacing water by anhydrous solvents of medium polarity has been proposed as a way to serve both needs. However, it was shown that the commonly employed glycosidases apparently need at least some water to remain active. (F. van Rantwijk et al., J. Mol. Catalysis B: Enzymatic 6:511-532, 1999). These diverging solvent requirements are difficult to satisfy. This is reflected in the elevated temperatures and long reaction times which the known methods for enzymatic glycoside synthesis in general require.

It was therefore an object of the present invention to develop a more effective method for the enzymatic production of ethylenically unsaturated glycosides. This may be achieved by increasing the reaction rate and/or by shifting the reaction equilibrium in favor of glycoside synthesis. Thus, a higher amount of product is obtained after a certain reaction time and/or when equilibrium is reached.

The inventors have now unexpectedly found that adding a non-reacting, water miscible organic solvent to a reaction mixture comprising saccharide, ethylenically unsaturated alcohol, glycosidase and water can significantly increase the amount of ethylenically unsaturated glycoside obtained after a certain reaction time.

Thus, the present invention provides a method for producing an ethylenically unsaturated glycoside of formula I

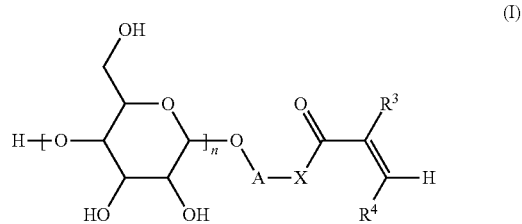

wherein
n is 1, 2 or 3;
A is $C_{2-20}$ alkylene or $-R^6-O-[-R^6-O-]_x-C_{2-20}$ alkylene;
X is selected from the group consisting of $-O-$, $-NH-$ and $-NR^5-$,
$R^3$ is selected from the group consisting of $-H$, and $C_{1-10}$ alkyl;
$R^4$ is selected from the group consisting of $-H$, $-COOH$ and $-COO^- M^+$;
$R^5$ is $C_{1-10}$ alkyl;
$R^6$ is H or $-CH_3$;
$M^+$ is selected from the group consisting of $Li^+$, $Na^+$, $K^+$ and $NH_4^+$; and
x is an integer of from 0 to 200;
comprising reacting an ethylenically unsaturated alcohol of formula II

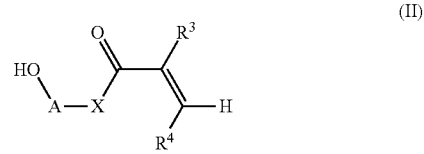

with a saccharide of formula III

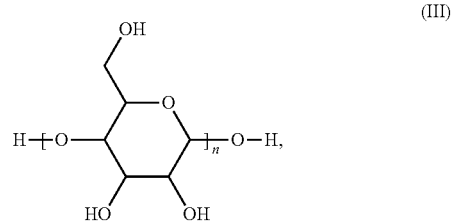

in the presence of a glycosidase
(i) at an initial molar ratio of ethylenically unsaturated alcohol of formula II to saccharide of formula III of from 2:1 to 30:1, for example from 15:1 to 25:1;
(ii) in the presence of a solvent mixture of water and a water miscible organic solvent that is no primary or secondary alcohol at a weight ratio of water to organic solvent of from 0.1:1 to 9:1, for example from 1:1 to 3:1; and (iii) at an initial weight ratio of solvent mixture to saccharide of from 3:1 to 30:1, for example from 10:1 to 20:1.

Definitions

The term "monosaccharide" as used herein refers to a single unit of a polyhydroxyaldehyde forming an intramolecular hemiacetal the structure of which including a six-membered ring of five carbon atoms and one oxygen atom. Monosaccharides may be present in different diasteromeric forms, such as α or β anomers, and D or L isomers. An "oligosaccharide" consists of short chains of covalently linked monosaccharide units. Oligosaccharides comprise disaccharides which include two monosaccharide units as well as trisaccharides which include three monosaccharide units. A "polysaccharide" consists of long chains of covalently linked monosaccharide units.

The term "glycosidic bond" or "glycosidic linkage" is a type of chemical bond or linkage formed between the anomeric hydroxyl group of a saccharide or saccharide derivative (glycone) and the hydroxyl group of another saccharide or a non-saccharide organic compound (aglycone) such as an alcohol. The reducing end of the di- or polysaccharide lies towards the last anomeric carbon of the structure, and the terminal end is in the opposite direction.

An "enzymatically catalyzed" or "biocatalytic" method as used herein means that said method is performed under the catalytic action of an enzyme, in particular of a glycosidase. The method can be performed in the presence of said glycosidase in isolated (purified, enriched) or crude form.

The term "glycosidase" also includes variants, mutants and enzymatically active portions of glycosidases.

Catalytic amounts of enzyme are expressed in "U" ("Unit" or "unit"), wherein 1 U equals the amount of enzyme which catalyses the reaction of 1 μmol substrate per minute under specific conditions (usually 37° C. and pH 7.5). Thus, 10 U glycosidase equals a catalytic amount of enzyme required for the reaction of 10 μmol saccharide substrate per minute. Catalytic amounts of maltogenic amylase can be expressed in "MANU" (Maltogenic Amylase Novo Unit), wherein 1 MANU equals the catalytic amount of enzyme required for the reaction of 1 μmol maltotriose per minute under standard conditions (10 mg/ml maltotriose, 37° C., pH 5.0, reaction time of 30 min). The catalytic amount of an enzyme can be determined by methods well known in the art.

The term "alkyl" comprises $C_{1-10}$ alkyl radicals which are linear or branched radicals having from 1 to 10 carbon atoms. Examples thereof are methyl, ethyl, n-propyl, isopropyl, n-butyl, 2-butyl, isobutyl or tent-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, nonyl, and decyl, as well as their constitutional isomers such as 2-ethylhexyl.

The term "alkylene" comprises $C_{2-20}$ alkylenediradicals which are linear or branched diradicals having from 1 to 20 carbon atoms.

The term "ethylenically unsaturated" refers to a compound comprising a non-aromatic C=C double bond. Specifically an "ethylenically unsaturated glycoside" as used herein refers to a glycoside consisting of a saccharide that is glycosidically linked to an ethylenically unsaturated alcohol.

A "water miscible organic solvent" is understood to mean an organic solvent that forms a homogeneous mixture with water at the weight ratio of water to organic solvent used.

The organic solvent is no primary or secondary alcohol and, accordingly, is non-reactive towards the saccharide. In general, the organic solvent is selected from the group consisting of alkanones, alkylnitriles, tertiary alcohols and cyclic ethers, and mixtures thereof.

Preferred solvents are selected from the group consisting of acetone, acetonitrile, t-pentanol, t-butanol, 1,4-dioxane and tetrahydrofuran, and mixtures thereof. 1,4-Dioxane is particularly preferred.

The ethylenically unsaturated alcohol of formula II is selected from
hydroxyalkyl(meth)acrylates;
N-hydroxyalkyl(meth)acrylamides; or
mono(hydroxyalkyl) esters of maleic acid or salts thereof.

In other embodiments the ethylenically unsaturated alcohol of formula II is an ethoxylated, propoxylated or ethoxylated and propoxylated derivative of the above ethylenically unsaturated alcohols.

Preferred ethylenically unsaturated alcohols of formula II are selected from 2-hydroxyethyl acrylate, 2-hydroxyethyl methacrylate, 3-hydroxypropyl acrylate, 3-hydroxypropyl methacrylate, N-(2-hydroxyethyl) acrylamide, N-(2-hydroxyethyl) methacrylamide, N-(3-hydroxypropyl) acrylamide, N-(3-hydroxypropyl) methacrylamide, (2-hydroxyethyl) hydrogen maleate.

In certain embodiments n is 1; A is $C_{2-6}$ alkylene; X is —O—; and $R^3$ is —H, or —$CH_3$.

The saccharide may be a monosaccharide such as glucose, galactose, or mannose; a disaccharide such as maltose, lactose or cellobiose; a trisaccharide such as maltotriose; or a mixture thereof. The method of the present invention does not require the saccharide to be activated, e.g. by the presence of an alkyl or o-nitrophenyl group linked via ether bond to the carbon atom at position 1 (C-1) of the saccharide. Suitably, the saccharide is selected from the group consisting of D-glucose, D-galactose, D-mannose, and mixtures thereof.

In the method of the present invention, the reaction of saccharide and ethylenically unsaturated alcohol is catalyzed by a glycosidase, a type of enzyme also known as glycoside hydrolase. Typically, enzymes show a high specificity regarding to the reactions they catalyze, the substrates that are involved in these reactions. Glycosidases are enzymes capable of catalyzing the hydrolysis of O- and S-glycosidic compounds. Further, glycosidases can be used for catalyzing the formation of glycosidic bonds through reverse hydrolysis, where the reaction equilibrium position is reversed, or transglycosylation, where a glycoside moiety is transferred from one glycoside, i.e. the donor glycoside, to another glycoside, i.e. the acceptor glycoside, to form a new glycoside. Glycosidases are assigned with enzyme classification number EC 3.2.1.x.

The glycosidase may be used in a purified form, as an enriched concentrate or as a crude enzyme preparation.

Suitably, the glycosidase present in the method of the invention is selected from the group consisting of amylases, cellulases, glucosidases and galactosidases.

α-Amylase is an enzyme having enzyme classification number EC 3.2.1.1, and is also known as glycogenase, endoamylase, Taka-amylase A, or 1,4-α-D-glucan glucanohydrolase. α-Amylases are capable of catalyzing the endohydrolysis of (1→4)-α-D-glucosidic linkages in polysaccharides containing three or more (1→4)-α-linked D-glucose units, such as starch and glycogen, thereby releasing reducing groups in the α-configuration.

β-Amylase is an enzyme assigned with enzyme classification number EC 3.2.1.2, and is also known as saccharogen amylase, glycogenase, or 1,4-α-D-glucan maltohydrolase. β-Amylases are capable of catalyzing the hydrolysis of (1→4)-α-D-glucosidic linkages in polysaccharides, such as starch and glycogen thereby releasing successive β-maltose units from the non-reducing ends of the polysaccharide chains.

Cellulase is an enzyme assigned with enzyme classification number EC 3.2.1.4, and is also known as endo-1,4-β-D-glucanase, β-1,4-glucanase, β-1,4-endoglucan hydrolase, celluase A, cellulosin AP, endoglucanase D, alkali cellulase, cellulase A 3, celludextrinase, 9.5 cellulase, avicelase, pancellase SS, or 1,4-(1,3;1,4)-β-D-glucan 4-glucanohydrolase. Cellulases are capable of catalyzing the endohydrolysis of (1→4)-β-D-glucosidic linkages in cellulose, lichenin and cereal β-D-glucans as well as 1,4-linkages in β-D-glucans also containing 1,3-linkages.

α-Glucosidase is an enzyme assigned with enzyme classification number EC 3.2.1.20, and is also known as maltase, glucoinvertase, glucosidosucrase, maltaseglucoamylase, α-glucopyranosidase, glucosidoinvertase, α-D-glucosidase, α-glucoside hydrolase, or α-1,4-glucosidase. α-Glucosidases are capable of catalyzing the hydrolysis of terminal, non-reducing (1→4)-linked α-D-glucose residues thereby releasing α-D-glucose.

β-Glucosidase is an enzyme assigned with enzyme classification number EC 3.2.1.21, and is also known as gentiobiase, cellobiase, emulsin, elaterase, aryl-β-glucosidase, β-D-glucosidase, β-glucoside glucohydrolase, arbutinase, amygdalinase, p-nitrophenyl β-glucosidase, primeverosidase, amygdalase, limarase, salicilinase, or β-1,6-glucosidase. β-Glucosidases are capable of catalyzing the hydrolysis of terminal, non-reducing β-D-glucosyl residues thereby releasing β-D-glucose.

α-Galactosidase is an enzyme assigned with enzyme classification number EC 3.2.1.22, and is also known as melibiase, α-D-galactosidase, α-galactosidase A, or α-galactoside galactohydrolase. α-Galactosidases are capable of catalyzing the hydrolysis of terminal, non-reducing α-D-galactose residues in α-D-galactosides, including galactose oligosaccharides, and galactomannans.

β-Galactosidase is an enzyme assigned with enzyme classification number EC 3.2.1.23, and is also known as lactase, β-lactosidase, maxilact, hydrolact, β-D-lactosidase, S 2107, lactozym, trilactase, β-D-galactanase, oryzatym, or sumiklat. β-Galactosidases are capable of catalyzing the hydrolysis of terminal non-reducing β-D-galactose residues in β-D-galactosides.

A crude form of glycosidase which is suitable for the method of the present invention is fruit seed meal. Fruit seed meals are robust and recyclable catalysts which can be produced in an easy and cost-effective way. Preparation and specific enzymatic activity of fruit seed meals has been described by Lu et al. (Practical methods for Biocatalysts, Whittall and Satton (eds.), Wiley, 2010, chapter 7.3, pages 236-239). The fruit seed meals which can be used in the method of the present invention comprise *Prunus dulcis* (almond) kernel meal, *Prunus persica* (peach) kernel meal, *Prunus armeniaca* (apricot) kernel meal, *Malus pumila* (apple) seed meal, and *Eriobotrya japonica* (loquat) seed meal. Preferably, the fruit seed meal used is selected from the group consisting of *Prunus dulcis* kernel meal, *Prunus persica* kernel meal, and *Malus pumila* seed meal.

The enzyme may be dissolved in the reaction mixture or immobilized on a solid support which is contacted with the reaction mixture. If the enzyme is immobilised, it is attached to an inert carrier. Suitable carrier materials are known in the art. Examples for suitable carrier materials are clays, clay minerals such as kaolinite, diatomeceous earth, perlite, silica, alumina, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For preparing carrier-bound enzymes the carrier materials usually are used in the form of fine powders, wherein porous forms are preferred. The particle size of the carrier material usually does not exceed 5 mm, in particular 2 mm. Further, suitable carrier materials are calcium alginate and carrageenan. Enzymes may directly be linked by glutaraldehyde. A wide range of immobilisation methods is known in the art (e.g. J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim).

The enzymatically catalyzed reaction can be carried out batch wise, semi-batch wise or continuously. Reactants can be supplied at the start of reaction or can be supplied subsequently, either semi-continuously or continuously. The catalytic amount of glycosidase required for the method of the invention depends on the reaction conditions, such as temperature, solvents and amount of substrate.

The reaction is performed in a solvent mixture of water and a water miscible organic solvent as described above. The reaction mixture may, but not have to, further comprise a suitable buffer in order to adjust the pH to a value of 6.0 to 9.0, for example in the range of 6.5 to 8.0, such as in the range of 7.0 to 7.8. Suitable buffers comprise, but are not limited to, sodium acetate, tris(hydroxymethyl)aminomethane ("TRIS") and phosphate buffers.

The concentration of the reactants, i.e. saccharide and ethylenically unsaturated alcohol, may be adapted to the optimum reaction conditions. For example, the initial saccharide concentration may be in the range of 100 mM to 3000 mM, for example 200 mM to 500 mM. One reactant, i.e. the ethylenically unsaturated alcohol, is used in molar excess in order to shift the reaction equilibrium to the side of the product.

The reaction temperature may be adapted to the optimum reaction conditions, which may depend on the specific enzyme applied. The reaction may expediently take place at temperatures between the freezing point of the reaction mixture and the denaturation temperature of the enzyme. Upon reaching the denaturation temperature the catalytic activity of the enzyme is lost. For example, the reaction may be performed at a temperature in the range from 0° C. to 80° C., for example 40° C. to 60° C. or at about 50° C.

The process may proceed until equilibrium between reactants and products is achieved, but may be stopped earlier. Usual process times are in the range from 6 h to 96 h, for example about 24 h.

The methodology of the present invention can further comprise a step of recovering the produced ethylenically unsaturated glycoside. The term "recovering" includes extracting, harvesting, isolating or purifying the compound from the reaction mixture. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like Thin Layer Chromatography (TLC), High Performance Liquid Chromatography (HPLC), gas chromatography (GC), Spectroscopy (e.g. IR, UV, NMR spectroscopy), coloring methods, NIRS, or enzymatic assays.

The examples described below are intended to illustrate the present invention without limiting it in any way.

Example 1

β-Glucosidase Catalyzed Synthesis of
2-(β-Glucosyloxy)-Ethyl Acrylate from D-Glucose 1.0 g D(+)-glucose was dissolved in 2 ml water. 12 ml 2-hydroxyethyl acrylate (containing 200 ppm MEHQ) and 1 ml 1,4-dioxane were added to the glucose solution. The reaction was started by addition of 0.070 g (364 U) R-glucosidase from Almonds. The reaction mixture was stirred for 24 h at 50° C. The product was detected by thin layer chromatography (TLC) (chloroform/methanol 4/1 (v/v), Rf 0.55) and purified by column chromatography (silica gel, eluant: chloroform/methanol 7/1 (v/v)). Fractions containing the aimed product were pooled and the solvent was removed by rotary evaporation. Yield: 0.459 g (46%). Purity: 99%

$^1$H-NMR δ in ppm: 3.2-4.2 GlucOCH$_2$CH$_2$R (8p); 4.39 GlucOCH$_2$CH$_2$R (2p Tri J 4.38 4.38 Hz); 4.50 GlucH$_a$ (1p Dou J 7.91 Hz); 5.99 H$_{trans}$CH=CHR (1p Dou J 10.46 Hz); 6.22 CH$_2$=CHR (1p DDou J 17.29 10.46 Hz); 6.46 H$_{cis}$CH=CHR (1p Dou J 17.30 Hz)

$^{13}$C-NMR δ in ppm: 60.9 GlucC$_6$·; 64.4 OCH$_2$CH$_2$; 68.1 OCH$_2$CH$_2$; 69.8 GlucC$_5$·; 73.3 GlucC$_2$·; 75.9 GlucC$_3$·; 76.1 GlucC$_4$·; 102.7 GlucC$_{1\beta}$·; 127.6 H$_2$C=CHR; 132.9 H$_2$C=CHR; 168.6 O(O)CR ESI-MS pos: calculated: 301.0894 (C11H18O8Na); observed: 301.2500

Example 2

β-Glucosidase Catalyzed Synthesis of
2-(β-Glucosyloxy)-Ethyl Methacrylate from D-Glucose 1.0 g D(+)-glucose was dissolved in 2 ml water. 12 ml 2-hydroxyethyl methacrylate (containing 200 ppm MEHQ) and 1 ml 1,4-dioxane were added to the glucose solution. The reaction was started by addition of 0.070 g (364 U) β-glucosidase from Almonds. The reaction mixture was stirred for 24 h at 50° C. The product was detected by TLC (chloroform/methanol 4/1 (v/v), Rf 0.59) and purified by column chromatography (silica gel, eluant: chloroform/methanol 7/1 (v/v)). Fractions containing the aimed product were pooled and the solvent was removed by rotary evaporation. Yield: 0.514 g (51%). Purity: 97%

$^1$H-NMR δ in ppm: 1.91 CH$_2$=C(CH$_3$)R (3p Sin); 3.2-4.2 GlucOCH$_2$CH$_2$R (8p); 4.35 GlucOCH$_2$CH$_2$R (2p Tri J 4.37 4.37 Hz); 4.48 GlucH$_a$ (1p Dou J 7.92 Hz); 5.70 H$_{trans}$CH=CCH$_3$R (1p Sin); 6.14 H$_{cis}$CH=CHCH$_3$R (1p Sin)

$^{13}$C-NMR δ in ppm: 17.5 H$_2$C=C(CH$_3$R; 60.8 GlucC$_6$·; 64.5 OCH$_2$CH$_2$; 68.1 OCH$_2$CH$_2$; 69.7 GlucC$_5$·; 73.2 GlucC$_2$·; 75.8 GlucC$_3$·; 76.1 GlucC$_4$·; 102.7 GlucC$_{1\beta}$·; 127.1 H$_2$O=C(CH$_3$)R; 135.9 H$_2$C=C(CH$_3$)R; 169.8 O(O)CR Example 3

β-Glucosidase Catalyzed Synthesis of
4-(β-Glucosyloxy)-Butyl Acrylate from D-Glucose 1.0 g D(+)-glucose was dissolved in 2 ml water. 12 ml 4-hydroxybutyl acrylate (containing 200 ppm MEHQ) and 1 ml 1,4-dioxane were added to the glucose solution. The reaction was started by addition of 0.070 g (364 U) R-glucosidase from Almonds. The reaction mixture was stirred for 24 h at 50° C. The product was detected by TLC (chloroform/methanol 4/1 (v/v), Rf 0.69) and purified by column chromatography (silica gel, eluant: chloroform/methanol 7/1 (v/v)). Fractions containing the aimed product were pooled and the solvent was removed by rotary evaporation. Yield: 0.310 g (31%). Purity (>85%)

$^1$H-NMR δ in ppm: 1.75 OCH$_2$CH$_2$CH$_2$CH$_2$O (4p); 3.2-4.2 GlucOCH$_2$CH$_2$R (8p); 4.21 (O)COCH$_2$R (2p Tri J 5.90 5.90 Hz); 4.43 GlucH$_a$ (1p Dou J 7.96 Hz); 5.95 H$_{trans}$CH=CHR (1p Dou J 10.43 Hz); 6.22 CH$_2$=CHR (1p DDou J 17.36 10.35 Hz); 6.41 H$_{cis}$CH=CHR (1p Dou J 17.32 Hz)

$^{13}$C-NMR δ in ppm: 24.7 OCH$_2$CH$_2$CH$_2$CH$_2$O; 25.6 OCH$_2$CH$_2$CH$_2$CH$_2$O; 61.0 GlucC$_5$·; 61.7 OCH$_2$R; 65.4 (O)COCH$_2$R; 69.9 GlucC$_5$·; 73.3 GlucC$_2$·; 76.0 GlucC$_3$·; 76.1 GlucC$_4$·; 102.4 GlucC$_{1\beta}$·; 127.9 H$_2$C=CHR; 132.4 H$_2$C=CHR; 168.9 RO(O)CR ESI-MS pos: calculated: 329.1207 (C13H22O8Na); observed: 329.1188

The invention claimed is:

1. A method for producing an ethylenically unsaturated glycoside of formula I

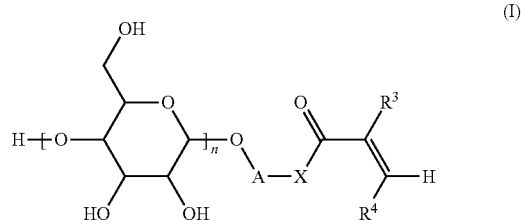

wherein
n is 1, 2 or 3;
A is $C_{2-20}$ alkylene or —R$^6$—O—[—R$^6$—O—]$_x$—C$_{2-20}$ alkylene;
X is selected from the group consisting of —O—, —NH— and —NR$^5$—,
R$^3$ is selected from the group consisting of —H, and $C_{1-10}$ alkyl;
R$^4$ is selected from the group consisting of —H, —COOH and —COO$^-$ M$^+$;
R$^5$ is $C_{1-10}$ alkyl;
R$^6$ is —C$_2$H$_4$— or —C$_3$H$_6$—;
M$^+$ is selected from the group consisting of Li$^+$, Na$^+$, K$^+$ and NH$_4^+$; and
x is an integer of from 0 to 200;
comprising reacting an ethylenically unsaturated alcohol of formula II

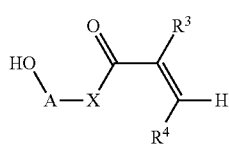

(II)

with a saccharide of formula III

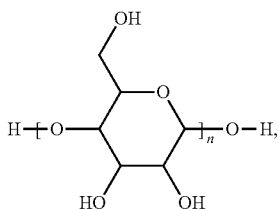

(III)

in the presence of a glucosidase
(i) at a molar ratio of ethylenically unsaturated alcohol of formula II to saccharide of formula III of from 2:1 to 30:1;
(ii) in the presence of a solvent mixture of water and 1,4-dioxane at a weight ratio of water to 1,4-dioxane of from 0.1:1 to 9:1; and
(iii) at a weight ratio of solvent mixture to saccharide of from 3:1 to 30:1.

2. The method of claim 1, wherein
A is $C_{2-6}$ alkylene;
X is —O—; and
$R^3$ is —H, or —CH$_3$.

3. The method of claim 2, wherein n=1.

4. The method of claim 1, wherein the saccharide is selected from the group consisting of D-glucose, D-galactose, D-mannose, and mixtures thereof.

5. The method of claim 1, wherein said ethylenically unsaturated alcohol of formula II is selected from the group consisting of a hydroxyalkyl(meth)acrylate, an N-hydroxyalkyl(meth)acrylamide, and a mono(hydroxyalkyl) ester of maleic acid, or a salt thereof.

6. The method of claim 1, wherein said ethylenically unsaturated alcohol of formula II is selected from the group consisting of an ethoxylated hydroxyalkyl(meth)acrylate, an ethoxylated N-hydroxyalkyl(meth)acrylamide, an ethoxylated mono(hydroxyalkyl) ester of maleic acid, a propoxylated hydroxyalkyl(meth)acrylate, a propoxylated N-hydroxyalkyl(meth)acrylamide, a propoxylated mono(hydroxyalkyl) ester of maleic acid, an ethoxylated and proptoxylated hydroxyalkyl(meth)acrylate, an ethoxylated and proptoxylated N-hydroxyalkyl(meth)acrylamide, an ethoxylated and proptoxylated mono(hydroxyalkyl) ester of maleic acid, or a salt thereof.

7. The method of claim 1, wherein said ethylenically unsaturated alcohol of formula II is selected from the group consisting of 2-hydroxyethyl acrylate, 2-hydroxyethyl methacrylate, 3-hydroxypropyl acrylate, 3-hydroxypropyl methacrylate, N-(2-hydroxyethyl)acrylamide, N-(2-hydroxyethyl)methacrylamide, N-(3-hydroxypropyl)acrylamide, N-(3-hydroxypropyl methacrylamide, and (2-hydroxyethyl)hydrogen maleate.

8. The method of claim 1, wherein said glucosidase is an α-glucosidase.

9. The method of claim 1, wherein said glucosidase is a β-glucosidase.

10. The method of claim 1, wherein said glucosidase is in a purified form, an enriched concentrate or a crude enzyme preparation.

11. The method of claim 1, wherein said glucosidase is dissolved into a reaction mixture of said ethylenically unsaturated alcohol of formula II and said saccharide of formula III.

12. The method of claim 1, wherein said glucosidase is immobilized on a solid support which is contacted with a reaction mixture of said ethylenically unsaturated alcohol of formula II and said saccharide of formula III.

13. The method of claim 12, wherein said solid support is an inert carrier.

14. The method of claim 12, wherein said solid support is a clay or a clay material.

15. The method of claim 12, wherein said solid support is a clay material selected from the group consisting of kaolinite, diatomeceous earth, perlite, silica, alumina, sodium carbonate, calcium carbonate, cellulose powder, anion exchanger materials, a synthetic polymer.

16. The method of claim 12, wherein said solid support is calcium alginate or carrageenan.

17. The method of claim 1, wherein said reacting is at a pH of 6.0 to 9.0.

18. The method of claim 1, wherein the initial saccharide concentration ranges from 100 mM to 3000 mM.

19. The method of claim 1, wherein said reacting is at a temperature of from 0° C. to 80° C.

20. The method of claim 1, wherein said reacting for a time ranging from 6 h to 96 h.

* * * * *